US00PP16600P2

(12) United States Plant Patent
Hall

(10) Patent No.: US PP16,600 P2
(45) Date of Patent: May 30, 2006

(54) ***LAVANDULA* PLANT NAMED 'LEMON LEIGH'**

(50) Latin Name: *Lavandula stoechas*
Varietal Denomination: Lemon Leigh

(76) Inventor: Elsie Hall, Leighvander, RD 1, Wairau Valley, Marlborough (NZ)

( * ) Notice: Subject to any disclaimer, the term of this patent is extended or adjusted under 35 U.S.C. 154(b) by 102 days.

(21) Appl. No.: 11/086,097

(22) Filed: Mar. 22, 2005

(51) Int. Cl.
*A01H 5/00* (2006.01)

(52) U.S. Cl. ..... Plt./226
(58) Field of Classification Search ..... Plt./226
See application file for complete search history.

*Primary Examiner*—Anne Marie Grunberg
(74) *Attorney, Agent, or Firm*—Mark P. Bourgeois

(57) ABSTRACT

A new cultivar of *Lavandula* plant named 'Lemon Leigh' that is characterized by large yellow green flowers, strong lemon scented leaves and light green foliage.

1 Drawing Sheet

Botanical classification: *Lavandula stoechas*.
Variety denomination: 'Lemon Leigh'.

BACKGROUND OF THE INVENTION

The present invention relates to a new and distinct cultivar of *Lavandula stoechas* and hereinafter referred to by the cultivar name 'Lemon Leigh'. The new cultivar was discovered growing in a cultivated area of Wairau Valley, Marlborough, New Zealand in 1998. The exact parents are unknown.

The new Lavender plant 'Lemon Leigh' is distinct and unique due to its large yellow green flowers, strong lemon scented leaves and light green foliage.

The closest comparison plant is *Lavandula* 'Viridis' (not patented). 'Lemon Leigh' is distinguishable from 'Viridis' by its larger leaves, longer crop time and light green leaves.

The new cultivar was first asexually propagated by cuttings in Wairau Valley, Marlborough, New Zealand by the inventor in 1998. Since that time, under careful observation, the unique characteristics of the new cultivar have been uniform, stable and reproduced true to type in successive generations of asexual reproduction.

SUMMARY OF THE INVENTION

The new lavender 'Lemon Leigh' is distinguished from other known varieties of *Lavandula,* by the following characteristics:

1. Large yellow green flowers
2. Strong lemon scented leaves
3. Light green foliage These unique traits set 'Lemon Leigh' apart from other existing varieties known to the inventor.

'Lemon Leigh' is distinguishable from *Lavandula* 'Viridis', by its larger leaves, longer crop time and light green leaves.

BRIEF DESCRIPTION OF THE DRAWINGS

The accompanying color photograph illustrates the distinguishing characteristics of the new cultivar 'Lemon Leigh'. The FIGURE shows the an overall view of a 3 month old plant. All photographs are taken using conventional photographic techniques and although foliage colors may appear different from actual colors due to light reflectance, they are as accurate as possible by conventional photography.

BOTANICAL DESCRIPTION OF THE PLANT

The following is a detailed description of the *Lavandula* cultivar named 'Lemon Leigh'. Data was collected in Wairau Valley, Marlborough, New Zealand from 3 month old plants. The plants were grown outdoors under natural conditions. The time of year was March. The temperature ranged from 12 to 30 degrees centigrade during the day and from 5 to 18 degrees centigrade at night. No growth retardant was used. Phenotypic differences may be observed with variations in environmental, climatic, and cultural conditions, without however, any difference in genotype. Color determinations are in accordance with The 1995 Royal Horticultural Society Colour Chart except where general color terms of ordinary dictionary significance are used. The growing requirements are similar to the species and no disease problems have been observed.

Botanical classification: *Lavandula stoechas* 'Lemon Leigh'.
Common name: Lavender
Parentage: The parents of 'Lemon Leigh' are unknown.
Type: Aromatic perennial shrub.
Use: Ornamental, hedge or back of border plant.
Growth rate: 20 cm. per month.
Habit: Rounded habit with erect, ascending flower spikes.
Height: 100 cm. in height.
Spread: 60 cm in width.
Hardiness: Zone 5 to zone 10.
Propagation method: Cuttings.
Vigor: Vigorous grower.
Root system: Fine and fibrous.
Soil: Plant in well-drained soil.
Light levels: Plant in full sun.
Special needs: None observed.
Time to initiate roots: 6 weeks from an unrooted cutting during the summer.
Time to produce a rooted cutting: 4 weeks during the summer.

Branching habit: Erect, upright, semi-open.
Pinching: No.
Internode length: 2 cm.
Stem:
*Shape.*—Cylindrical.
*Surface.*—Puberulent.
*Color.*—146B.
*Size.*—Average 4 mm in diameter, 30 cm in length.
*Strength.*—Strong.
Foliage:
*Arrangement.*—Erect stems with whorls of leaves, arranged opposite along stem, a basal pair of leaves subtend each whorl.
*Leaf dimensions.*—4.5 cm. in length and 4 mm. in diameter.
*Leaf division.*—Simple.
*Apex.*—Acute.
*Base.*—Truncate.
*Margins.*—Entire.
*Leaf shape.*—Linear.
*Color of mature leaves* (*upper and lower surfaces*).—146B.
*Color of young leaves* (*upper and lower surfaces*).—146B.
*Upper and lower surfaces.*—Puberulent.
*Foliar fragrance.*—Strong lemon scent.
*Petiole.*—Sessile.
*Length.*—2 cm. in length.
*Width.*—3 mm. in width.
Flower:
*Flowering habit.*—Spring to summer continuously.
*Type of inflorescence.*—Terminal spike.
*Shape of inflorescence.*—Cylindrical-conic fusiform.
*Spike size.*—7 cm. in height and 2 cm. in width.
*Flower shape.*—Tubular
*Flower size.*—2 cm. in length and 10 mm in diameter.
*Corolla shape.*—Two-lipped with upper lip 2-lobed and lower lip 3-lobed.
*Corolla color.*—151A.
*Calyx shape.*—Two-lipped with upper lip 2-lobed.
*Calyx color.*—151A.
*Calyx surface.*—Pubescent.
*Bracts.*—5 in number.
*Bract shape.*—Oblanceolate with undulating margins.
*Bract dimensions.*—28 mm. in length and 6 mm. in width.
*Bract color.*—151A.
*Bud length.*—25 mm.
*Bud diameter.*—6 mm.
*Bud color.*—90A.
*Flower longevity.*—21 to 25 days.
*Flower longevity as a cut flower.*—7 days.
Peduncle:
*Peduncle length.*—8 cm.
*Peduncle diameter.*—2 mm.
*Peduncle strength.*—Strong.
*Peduncle color.*—144B.
Reproductive organs: Have not been observed.
Seed production: Has not been observed.
Disease and pest resistance: Has not been observed.

What is claimed is:

1. A new and distinct variety of *Lavandula* plant named 'Lemon Leigh' as described and illustrated.

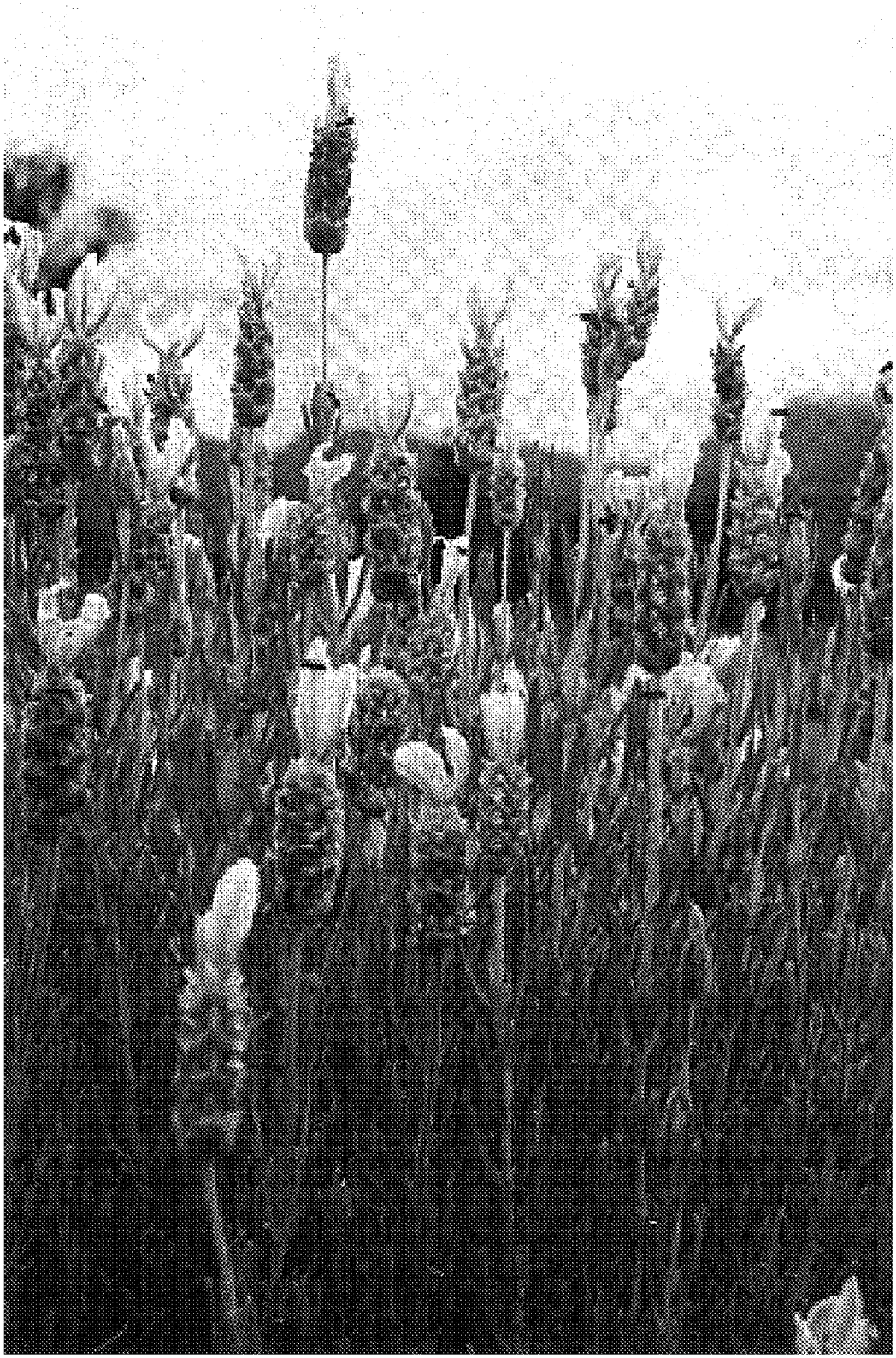

* * * * *